United States Patent [19]

Fried

[11] Patent Number: 5,155,279
[45] Date of Patent: Oct. 13, 1992

[54] PROCESS FOR THE OXIDATION OF ALCOHOLS TO ALDEHYDES

[75] Inventor: Herbert E. Fried, Houston, Tex.

[73] Assignee: Shell Oil Company, Houston, Tex.

[21] Appl. No.: 776,777

[22] Filed: Oct. 18, 1991

[51] Int. Cl.$^5$ .................. C07C 45/38; C07C 45/39
[52] U.S. Cl. .................... 568/471; 568/426; 568/436; 568/442; 568/449; 568/470
[58] Field of Search .......... 568/426, 449, 470, 471, 568/472, 485, 486, 487, 455, 436, 442

[56] References Cited

U.S. PATENT DOCUMENTS 4,620,033 10/1986 Isshiki et al. ............... 562/519

FOREIGN PATENT DOCUMENTS 5096516 11/1986 Japan.

OTHER PUBLICATIONS

"J. Organic Chem." vol. 52 (12) pp. 2559–2562.
"J. Organic Chem." vol. 55 pp. 462–466 (1990).
"J. Amer. Chem. Soc." vol. 106 p. 3374 (1984).
Miyazawa et al., "Oxidation of Benzyl Alcohol with Iron(III) Using Polymers Containing Nitroxyl Radical Structure as a Mediator," J. Polym. Sci., Polym. Chem. Ed., 23(9), 1985, pp. 2487–2494.
Grigor'ev et al., "Participation of Nitroxyl Radical in the Oxidation of Aldehyde and Alcohol Groups in 3–imidazolin–1–oxyls," Izc. Akad. Nauk SSSR, Ser. Khim., (1), 1978, pp. 208–210.
Miyazawa et al., "Oxidation of Benzyl Alcohol with Copper(II) Mediated by a Polymeric Oxoaminium Salt," J. Mol. Catal., 49(1), 1988, 131–134.
Ganem et al., "Biological Spin Labels as Organic Reagents. Oxidation of Alcohols to Carbonyl Compounds Using Nitroxyls," J. Org. Chem., 40(13), 1975, pp. 1998–2000.
Miyazawa et al., "Oxidation of Benzyl Alcohol by Iron-(III) Mediated by Nitroxyl Radical," J. Mol. Catal., 31(2), 1985, pp. 217–220.
Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559–2562.
Inokuchi et al., "A Selective and Efficient Method for Alcohol Oxidations Mediated by N–Oxoammonium Salts in Combination with Sodium Bromite," J. Org. Chem., 1990, 55, pp. 462–466.
Organic Synthesis, vol. 69, p. 212 (1990).
Semmelhack et al., "Oxidation of Alcohols to Aldehydes with Oxygen and Cupric Ion, Mediated by Nitrosonium Ion," J. Am. Chem. Soc. 1984, 106, 3374–3376.
Yamaguchi et al., "Application of Redox System Based on Nitroxides to Organic Synthesis," Pure & Applied Chemistry, vol. 62(2), 1990, pp. 217–222.

*Primary Examiner*—Werren B. Lone
*Attorney, Agent, or Firm*—Pamela J. McCollough

[57] ABSTRACT

A process for the preparation of an aldehyde which comprises reacting the corresponding alkanol with a solubilized stable free radical nitroxide having the formula:

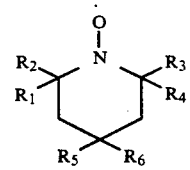

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid and a solvent, in the absence of an oxidant at a temperature in the range of from about $-10°$ C. to about $60°$ C. and thereafter separating out the aldehyde.

12 Claims, No Drawings

PROCESS FOR THE OXIDATION OF ALCOHOLS TO ALDEHYDES

FIELD OF THE INVENTION

This invention relates to a process for the preparation of aldehydes by the oxidation of the corresponding alcohols in the presence of a stable free radical nitroxide, nitric acid and a solvent in the absence of an oxidant.

BACKGROUND OF THE INVENTION

It is known to use nitroxyl radicals/oxoammonium salts in the oxidation of primary alcohols to produce aldehydes and acids and secondary alcohols to produce ketones (*Journal of Organic Chemistry*, vol. 52 (12), pp. 2559-2562 and *Journal of Organic Chemistry*, vol. 55, 1990, pp. 462-466).

It is reported in the open literature that primary aliphatic alcohols can be converted to aldehydes in 30-40% yields in the presence of catalytic amounts of cuprous chloride, 2,2,6,6,-tetramethylpiperidine-1-oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217-222).

OBJECTS OF THE INVENTION

It is an object of this invention to produce aldehydes with high selectivities from alkanols without producing large amounts of other products such as acids and esters.

It has been found that the selectivity to aldehydes can be improved by using catalytic amounts of a stable free radical nitroxide and nitric acid in the absence of an oxidant.

SUMMARY OF THE INVENTION

This invention relates to a process for the preparation of an aldehyde which comprises reacting the corresponding alkanol with a solubilized stable free radical nitroxide having the formula:

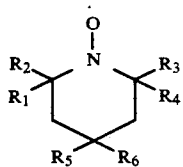

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid, and a solvent in the absence of an oxidant for less than about eight hours at a temperature in the range of from about $-10°$ C. to about 60° C., and thereafter separating out the aldehyde.

DESCRIPTION OF THE PREFERRED EMBODIMENTS

The present process converts alkanols to the corresponding aldehydes by contacting the alkanol with a solubilized stable free radical nitroxide, nitric acid and a solvent at a temperature in the range of from about $-10°$ C. to about 60° C. in the absence of an oxidant.

The alkanol reactant suitably comprises one or more alkanols having a carbon number in the range of from about 1 to about 45. An alkanol consisting essentially of primary, mono-alkanols is preferred. Most preferably, the alkanol reactant consists essentially of one or more $C_6$ to $C_{30}$ primary mono-alkanols. Preference can also be expressed for alkanols having from 8 to about 20 carbon atoms, with $C_9$ to $C_{18}$ alkanols considered more preferred and $C_{11}$ to $C_{18}$ alkanols considered most preferred. As a general rule, the carbon chains of the alkanols may be of either branched or linear (straight-chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such alkanols as reactants in oxidation reactions is well recognized in the art. Examples of specific alkanols and of commercially available alkanols and alkanol mixtures within this class are also well known. Commercially available mixtures of primary mono-alkanols prepared via the oligomerization of ethylene and the hydroformylation or oxidation and hydrolysis of the resulting higher olefins are particularly preferred.

Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418)., and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkanols to the corresponding aldehydes. These catalysts are generated in situ by the oxidation of a stable free radical nitroxide to an oxoammonium salt with nitric acid. The stable free radical nitroxide can be obtained by the oxidation of secondary amines or hydroxylamines.

The stable free radical nitroxides which are suitable for use in the instant invention have the formula:

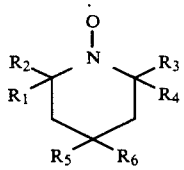

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alkyl, hydrogen, aryl or a substituted hexeroatom. As used herein, the term "alkyl" is meant to include cycloalkyl. The alkyl (or heteroatom substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the heteroatom substituents may include, halogen, oxygen, nitrogen and the like. Preferably, one of $R_5$ and $R_6$ is hydrogen while the other is a heteroatom which does not interfere with the reaction. Suitable substituted heteroatoms include —OR,

—$NME_3Cl^-$, O—$SO_3H$, —O— polymer and the like.

In a preferred embodiment, the nitroxide is selected from the group consisting of 2,2,6,6-tetramethyl-piperidine-1-oxyl, 4-hydroxy-2,2,6, 6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

As used herein, the term "nitric acid" refers to nitric acid or fuming nitric acid. The nitric acid suitable for use in the present invention typically has a concentration in the range of from about 50 percent to about 100 percent, preferably about 70 percent. Generally, an amount of nitric acid in the range of from about 5 mole percent to about 100 mole percent, basis the number of moles of starting alkanol is used. The nitric acid is typically added to the reaction mixture after all of the other reactants have been added.

The process of the present invention must be carried out in the absence of an oxidant in order to obtain the desired aldehyde products. When the process is carried out in the presence of an oxidant, carboxylic acids, rather than aldehydes, become the major products.

The reaction in the present invention is carried out utilizing a solubilized free radical nitroxide. The solvent is generally one in which the alkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, dichloromethane, sulfolane, acetone, monoglyme, dimethyl formamide, N-methylpyrrolidone, ethyl acetate, tertiary alcohols such as tertiary butyl alcohol, and mixtures thereof. In a preferred embodiment, the solvent is selected from acetonitrile, dichloromethane and mixtures thereof. The amount of solvent utilized in the process is typically in the range of from about 20:1 to about 0.5:1, preferably from about 10:1 to about 3:1, basis the weight of the starting alkanol.

The amounts and concentrations of the reactants utilized in the process of the instant invention can vary within wide ranges. The amount of stable free radical nitroxide is typically in the range of from about 1 mole percent by weight to about 50 mole percent, preferably from about 5 mole percent by weight to about 20 percent, basis the number of moles of starting alkanol. Generally, the amount of nitric acid is in the range of from about 5 mole percent to about 100 mole percent, preferably from about 25 mole percent to about 50 mole percent, basis the number of moles of the starting alkanol.

The process of the present invention is typically conducted under mild conditions, with good results being obtained using a temperature in the range of from about $-10°$ C. to about $60°$ C., and preferably in the range of from about $20°$ C. to about $40°$ C. Reaction pressures are not critical. The time required for the reaction to proceed to aldehydes is somewhat dependent on the temperature and the concentrations of the reactants. The optimum times for maximizing the selectivity to aldehydes using a particular solvent can be readily determined by one skilled in the art with a minimal amount of routine experimentation. Extended reaction times, however, can lead to dimerization of the desired aldehydes.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of alkanol, 0.006 moles of the nitroxide, and solvent may be added to the reaction vessel under a nitrogen atmosphere, followed by the addition of 0.016 moles of 70 percent nitric acid the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as, for example, distillation.

Depending upon process conditions and the nitroxide used, the selectivity to aldehyde obtained by this invention can be greater than about 65% of the starting alkanol. The products produced by the instant process can be used in a variety of applications. For example, these products can be used as intermediates in the preparation of esters, acetals, imines, amines and acids.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

6 Grams of 1-dodecanol, 1 gram of 2,2,6,6-tetramethyl-piperidine-1-oxyl and 25 milliliters of acetonitrile were charged to a 100 milliliter round bottomed flask under nitrogen atmosphere. To this mixture was added 1 gram of 70% nitric acid. The reaction was maintained in a nitrogen atmosphere at 35° C. over a 6 hour period. The results are presented in Table I.

Example 2

6 Grams of 1-dodecanol, 1 gram of 2,2,6,6-tetramethylpiperidine-1-oxyl, 25 milliliters of dichloromethane, and 0.25 grams of potassium bromide in 1 gram of water were charged to a 100 milliliter round bottomed flask under a nitrogen atmosphere. To this mixture was added 1 gram of 70% nitric acid. The reaction was maintained in a nitrogen atmosphere at a temperature of 35° C. over a 4 hour period. The results are presented in Table I.

Example 3

6.0 Grams of 1-dodecanol, gram of 2,2,6,6-tetramethyl-piperidine-1-oxyl and 25 milliliters of acetonitrile were charged to a 100 milliliter round bottomed flask under a nitrogen atmosphere. To this mixture was added 1 gram of 70% nitric acid. The reaction was maintained in a nitrogen atmosphere at room temperature over a 4 hour period. The results are presented in Table I.

Comparative Example A

Comparative Example A was carried out in a manner similar to Example 1 except that a stream of $O_2$ was bubbled through the reaction mixture. The results are presented in Table I.

Comparative Example B

Comparative Example B was carried out in a manner similar to Example 2 except that a stream of $O_2$ was bubbled through the reaction mixture. The results are presented in Table I.

As can be seen in Table I, the presence of oxygen results in the formation of large amounts of acids rather than the desired aldehydes.

TABLE I

| Oxidation Of Alkanols to Aldehydes | | | | |
|---|---|---|---|---|
| | % Conversion | % Sel. Aldehydes | % Sel. Dimers | % Sel. Acids |
| Example 1 | 84 | 71 | 2 | 27 |
| Example 2 | 54 | 69 | 29 | 2 |
| Example 3 | 42 | 81 | 19 | 0 |
| Comparative Example A | >99 | 33 | 3 | 64 |
| Comparative Example B | >99 | 3 | 7 | 90 |

TABLE I-continued

| Oxidation Of Alkanols to Aldehydes | | | | |
|---|---|---|---|---|
| | % Conversion | % Sel. Aldehydes | % Sel. Dimers | % Sel. Acids |
| Example B | | | | |

What is claimed is:

1. A process for the preparation of an aldehyde which comprises reacting the corresponding alkano having a carbon number in the range of from about 1 to about 45 with a solubilized stable free radical nitroxide having the formula:

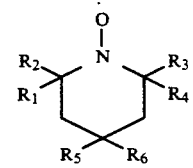

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid and a solvent selected from the group consisting of acetonitrile, dichloromethane, sulfolane, acetone, monoglyme, dimethyl formamide, N-methyl pyrrolidone, tertiary butyl alcohol, tertiary amyl alcohol, ethyl acetate and mixtures thereof, in the absence of an oxidant at a temperature in the range of from about $-10°$ C. to about 60° C. and thereafter separating out the aldehyde.

2. The process of claim 1 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein said a solvent selected from the group consisting of acetonitrile, dichloromethane and mixtures thereof.

5. The process of claim 1 wherein said is nitric acid has a concentration in the range of from about 50 percent to about 100 percent.

6. The process of claim 5 wherein said nitric acid has a concentration of about 70 percent.

7. The process of claim 1 wherein said the amount of nitric acid utilized is in the range of from about 5 mole percent to about 100 mole percent.

8. The process of claim 1 wherein said alkanol is contacted with said solubilized stable free radical nitroxide, followed by the addition thereto of said nitric acid.

9. The process of claim 8 wherein the amount of solubilized stable free radical nitroxide is in the range of from about 1 mole percent to about 50 mole percent, basis the number of moles of said alkanol.

10. The process of claim 8 wherein the amount of solubilized stable free radical nitroxide is in the range of from 5 mole percent to about 20 mole percent, basis the number of moles of said alkanol.

11. The process of claim 8 wherein wherein said the amount of nitric acid utilized is in the range of from about 5 mole percent to about 100 mole percent.

12. The process of claim 1 wherein said process is carried out at a temperature in the range of from about 20° C. to about 40° C. and at atmospheric pressure.

* * * * *